(12) United States Patent
Eppes

(10) Patent No.: US 6,599,762 B1
(45) Date of Patent: Jul. 29, 2003

(54) DEFECT DETECTION USING LIQUID CRYSTAL AND INTERNAL HEAT SOURCE

(75) Inventor: David Harry Eppes, Austin, TX (US)

(73) Assignee: Advanced Micro Devices, Inc., Sunnyvale, CA (US)

(*) Notice: Subject to any disclaimer, the term of this patent is extended or adjusted under 35 U.S.C. 154(b) by 0 days.

(21) Appl. No.: 09/521,627

(22) Filed: Mar. 8, 2000

(51) Int. Cl.[7] ............................................. H01L 21/66
(52) U.S. Cl. ........................ 438/14; 438/10; 438/16; 324/750; 324/753
(58) Field of Search ..................... 438/5, 6, 7, 10, 438/11, 14, 15, 16, 17, 18; 324/750, 755, 760, 770, 753

(56) References Cited

U.S. PATENT DOCUMENTS

| | | | |
|---|---|---|---|
| 5,008,617 A | * 4/1991 | Czubatyj et al. | 438/17 |
| 5,258,705 A | * 11/1993 | Okamoto et al. | 324/770 |
| 5,394,098 A | * 2/1995 | Meyrueix et al. | 324/750 |
| 5,504,017 A | * 4/1996 | Yue et al. | 438/17 |
| 5,777,487 A | * 7/1998 | Burgess et al. | 324/765 |
| 5,804,980 A | * 9/1998 | Nikawa | 324/752 |
| 5,963,040 A | * 10/1999 | Liu | 324/551 |
| 6,121,059 A | * 9/2000 | Liu | 438/14 |
| 6,403,386 B1 | * 6/2002 | Liu | 438/14 |

OTHER PUBLICATIONS

D. L. Burgess and O. D. Trapp, *Failure and Yield Analysis Handbook*, Oct. 1992, pp. 7.9–7.16.
D. Burgess, *Electronic Failure Analysis: Seminar Reference, Liquid Crystal Hot Spot Detection*, ASM International, 1998, pp. 143–145.
*Failure Analysis of Integrated Circuits: Tools and Techniques*, Lawrence C. Wagner, Ed., 1999, pp. 70–77.
Khandekar, S and Wills, K.S., *Micro Electronic Failure Analysis: Liquid Crystal Microscopy*, ASM International, 1993, pp. 141–144.

* cited by examiner

Primary Examiner—Kevin M. Picardat

(57) ABSTRACT

Defect analysis of an integrated circuit die having an internal heat source is enhanced using a method and system that use the internal heat source to heat the die. According to an example embodiment of the present invention, a semiconductor die having a liquid crystal layer is analyzed by detecting a liquid crystal phase change caused by electrical operation of the die. A first circuit region is electrically operated and used as the primary heat source to generate sufficient heat at a second circuit region to effect a separately viewable phase change in an area of the liquid crystal layer corresponding to the second circuit region. The internal heat source is adapted to cause the liquid crystal phase change without necessarily heating the die with an external heat source. A detector is adapted and used to detect the liquid crystal phase change in the area corresponding to the second circuit region.

43 Claims, 5 Drawing Sheets

DEFECT DETECTION USING LIQUID CRYSTAL AND INTERNAL HEAT SOURCE

FIELD OF THE INVENTION

The present invention relates generally to semiconductor devices and their fabrication and, more particularly, to semiconductor devices and their manufacture involving techniques for analyzing and debugging circuitry within an integrated circuit.

BACKGROUND OF THE INVENTION

The semiconductor industry has recently experienced technological advances that have permitted dramatic increases in circuit density and complexity, and equally dramatic decreases in power consumption and package sizes. Present semiconductor technology now permits single-chip microprocessors with many millions of transistors, operating at speeds of hundreds of millions of instructions per second to be packaged in relatively small, air-cooled semiconductor device packages. A by-product of such high-density and high functionality in semiconductor devices has been the demand for increased numbers of external electrical connections to be present on the exterior of the die and on the exterior of the semiconductor packages which receive the die, for connecting the packaged device to external systems, such as a printed circuit board.

As the manufacturing processes for semiconductor devices and integrated circuits (IC) increase in difficulty, methods for testing and debugging these devices become increasingly important. Not only is it important to ensure that individual chips are functional, it is also important to ensure that batches of chips perform consistently. In addition, the ability to detect a defective manufacturing process early is helpful for reducing the number of defective devices manufactured.

One IC analysis method involves using a liquid crystal material. Liquid crystalline materials have both crystalline solid and liquid characteristics. These characteristics enable their use for thermally analyzing an integrated circuit for defects. When the liquid crystal material is heated, its properties change. These changes include, for example, a coloring change and an ordering transition. Available defect analysis methods use the changes as indications of temperature in an integrated circuit. Detecting the temperature and temperature variations of an IC is useful for detecting circuit defects that result in excessive current drain and, therefore generate excessive heat. By forming a liquid crystal layer on an integrated circuit, the response of the liquid crystal can be monitored and used to detect such "hot spots" that are an indication of a defect.

One type of liquid crystalline material useful for defect analysis is calamatic liquid crystal material having nematic ordering. Calamatic liquid crystals have long, rod-shaped molecules, and those having nematic ordering change under temperature variation from a nematic to an isotropic state. In the nematic state, the liquid crystal alters the polarization of light incident upon it. When the liquid crystal changes to an isotropic state, the polarization of incident light is no longer affected. This change in the effect upon incident light is used to detect a temperature change in the liquid crystal material. The transition temperature at which the change occurs is dependent upon the particular characteristics of the material.

Typical analysis methods that use liquid crystals involve forming a liquid crystal layer on an integrated circuit, heating the circuit with an external source, and observing a change in the state of the liquid crystal. The liquid crystal layer is often formed by adding a solvent, such as pentane, to the liquid crystal material and then applying the material to the surface of an integrated circuit device with an eyedropper. The solvent evaporates, leaving the liquid crystal material behind. Other liquid crystal application methods include applying liquid crystal with a spreading strip, or applying a drop of liquid crystal on the chip and spinning the chip to spread out the liquid crystal. In addition, a liquid crystal emulsion may be used in place of the liquid crystal mixed with a solvent.

Once the liquid crystal has been applied, the integrated circuit is then heated with an external heater. The heater is used to bring the integrated circuit to within about 0.1 Kelvin of the transition temperature of the liquid crystal material. A microscope is directed at the liquid crystal layer. A suitable microscope includes a polarized light source and a linear polarizer (analyzer) in front of an eyepiece or camera. The integrated circuit is electrically stimulated, thereby heating a defect in the circuit and raising the liquid crystal material over the defect to its transition temperature. The liquid crystal material changes from nematic to isotropic phase, which is evidenced by a dark spot that is detected by the microscope.

One problem with currently used methods for liquid crystal IC analysis is associated with the need to externally heat the IC. Using an external heat source adds to the complexity of the integrated circuit analysis. In addition, the external heat source may not be capable of obtaining a particular heating pattern within the die. For example, in certain applications, it is desirable to generate more heat in a particular region of the die relative to the heat generated in the rest of the die.

Another problem is associated with internal intrinsic heat sources that generate so much heat when powered that they tend to overwhelm defect-related heat sources in certain types of ICs. Typical intrinsic heat sources, such as phase lock loops (PLL) and crystal oscillators, generate heat during normal operation that is significantly greater than heat generated by surrounding circuitry. These intrinsic heat sources make liquid crystal analysis of defective ICs difficult because the intrinsic heat causes the liquid crystal to change phase at such a rate that liquid crystal phase changes due to defects are difficult or impossible to detect using conventional methods. It would be beneficial to be able to heat an IC die for analysis without using an external heat source and while maintaining the capability to detect defects in the presence of intrinsic heat sources that generate significant heat.

SUMMARY OF THE INVENTION

The present invention is directed to a method and system for addressing the above-mentioned problems, as well as other problems, associated with defect detection in an IC die using liquid crystal. The defect detection can be used without necessarily using an external heat source, and can be used to detect defects in dies having intrinsic heat sources that make conventional liquid crystal analysis difficult or even impossible. The present invention is exemplified in a number of implementations and applications, some of which are summarized below.

According to an example embodiment of the present invention, a first circuit region in semiconductor die having a liquid crystal layer is electrically operated to generate heat in the die and cause a liquid crystal phase change without applying an external heat source to the die. The first circuit region is electrically operated and, in conjunction with heat generated at a second circuit region, effects a separately detectable phase change in a corresponding area of the liquid crystal layer. The liquid crystal phase change in the area corresponding to the second circuit region is detected and used for analyzing the die, such as for detecting a defect in the second circuit region.

The above summary of the present invention is not intended to describe each illustrated embodiment or every implementation of the present invention. The figures and detailed description that follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1A:
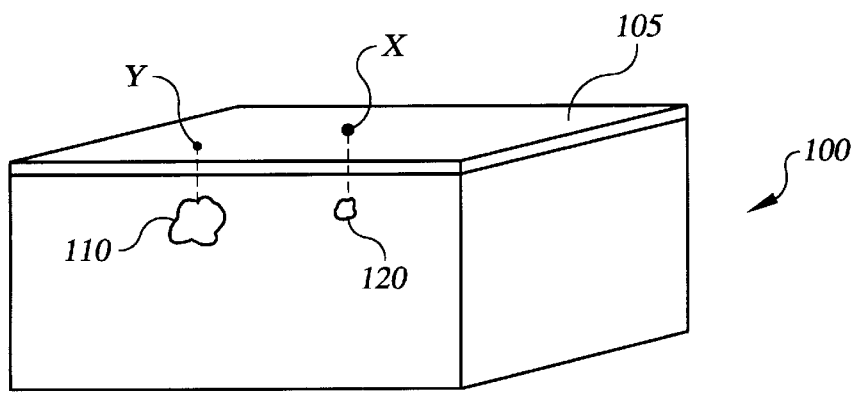
FIG. 1A is a semiconductor die having a liquid crystal layer, for use in accordance with an example embodiment of the present invention.

While the invention is amenable to various modifications and alternative forms, specifics thereof have been shown by way of example in the drawings and will be described in detail. It should be understood, however, that the intention is not necessarily to limit the invention to the particular embodiments described. On the contrary, the intention is to cover all modifications, equivalents, and alternatives falling within the spirit and scope of the invention as defined by the appended claims.

DETAILED DESCRIPTION

The present invention is believed to be applicable for a variety of different types of semiconductor devices, and the invention has been found to be particularly suited for dies requiring or benefiting from defect analysis involving the detection of heat that causes liquid crystal to change phase. While the present invention is not necessarily limited to such devices, various aspects of the invention may be appreciated through a discussion of various examples using this context.

In connection with an example embodiment of the present invention, it has been discovered that liquid crystal analysis can be performed on particular IC dies having internal heat sources that, when powered, sufficiently heat to cause a liquid crystal phase change without necessarily heating the die with an external heat source. The internal heat sources may be intrinsic, or may be formed in the die for defect analysis requiring heat generation.

In one example embodiment, liquid crystal is formed on the die, and the die is powered. As the die heats, the portion of the die having a defect heats faster than the surrounding area, and the liquid crystal formed over the die is heated by the heat from the defect. As the liquid crystal reaches its transition temperature it changes phase, and the phase change is detected and used to detect the defect. This is useful for eliminating the external heating component of liquid crystal analysis systems and methods.

In some instances, an intrinsic heat source can generate so much heat that liquid crystal analysis of defects using conventional detection methods is inhibited or even prevented. This is so because the heat generated at the intrinsic source can overwhelm the heat generated by defects, making a defect-generated liquid crystal phase change difficult to detect. The intrinsic-generated heat can cause the liquid crystal to transition so fast that a defect-generated liquid crystal phase change cannot be detected using conventional means. However, in connection with another example embodiment of the present invention, it has been discovered that the overwhelming heat generated by the intrinsic heat source can be overcome. For example, when the liquid crystal phase change due to the defect occurs at a very short time interval before the phase change due to the overwhelming heat from the intrinsic heat source occurs, the separate phase changes can be detected using time-lapsed analysis. For more information regarding time-lapsed analysis, reference may be made to U.S. patent application Ser. No. 09/521,260, entitled "Time-lapsed IC Defect Analysis Using Liquid Crystal," and filed concurrently herewith. In this instance, an image of the liquid crystal phase change can be recorded and reviewed in slow motion to detect the liquid crystal phase change due to the defect.

Another manner in which to overcome the overwhelming heat generated by an intrinsic heat source is to cool the die to slow the heat generated at the intrinsic heat source. This allows the heat generated by the defect to be separately detected. Cooling the die can be particularly useful when the heat generated by the intrinsic heat source is so overwhelming that the liquid crystal nearest the defect changes phase due to the intrinsic heat before the heat from the defect can affect it. By cooling the die, the progression of the liquid crystal phase change can be slowed or even reversed.

According to another example embodiment of the present invention, a semiconductor die having a liquid crystal layer is analyzed. A first circuit region is electrically operated, and the electrical operation causes the first circuit region and a second circuit region to effect a separately viewable phase change in corresponding areas of the liquid crystal layer. The first and second circuit regions are selected such that the corresponding phase changes cease to be separately viewable by conventional methods, such as by viewing the real-time phase change through a microscope. A detector is adapted and used to detect the liquid crystal phase change in the area corresponding to the second circuit region before the corresponding areas cease to be separately viewable. In this manner, defects can be located in die circuitry that has a significant intrinsic heat source that overwhelms defect related heat sources.

Figure 1B:
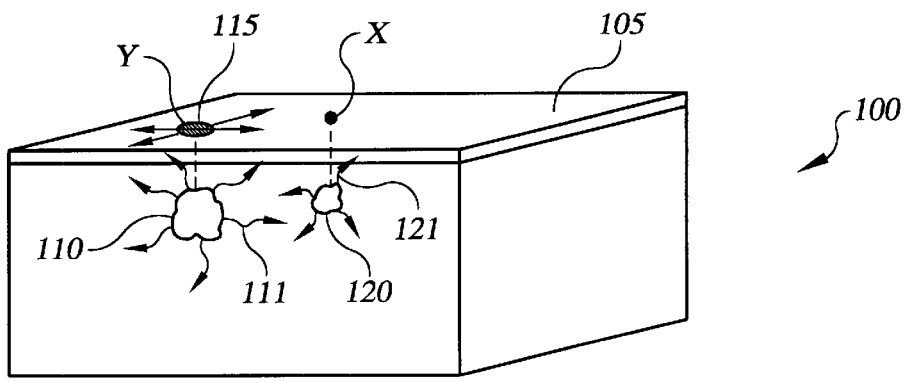
FIG. 1B is the semiconductor die of FIG. 1A undergoing analysis, according to an example embodiment of the present invention.

For example, FIGS. 1A and 1B show a semiconductor die 100 undergoing liquid crystal analysis, according to an example embodiment of the present invention. The die has a first circuit region 110 and a second circuit region 120. A layer of liquid crystal material 105 having a transition temperature is formed over the die. Portions Y and X of the liquid crystal layer are located over the first and second circuit regions 10 and 120, respectively. The die is electrically operated at FIG. 2, and heat is generated in the die. The heat 111 generated at circuit region 10 is greater than and tends to overwhelm the effect of the heat 121 generated at circuit region 120. As the heat spreads from the circuit regions, the temperature of the surrounding portions of the die increases. The liquid crystal layer is also heated, and when it reaches its transition temperature, it undergoes a phase change viewable as a dark spot.

As the circuit region 110 generates heat, portion Y of the liquid crystal reaches its transition temperature and undergoes a phase change. The liquid crystal phase change beginning at portion Y expands radially, and the radial expansion has a leading edge 115. The heat from both of the circuit regions also reaches liquid crystal portion X. Since portion X is being heated by both circuit regions, it changes phase momentarily before the leading edge 115 of the expanding liquid crystal phase change reaches it. The selected circuit regions are so close that the phase change at portion X occurs at such a short time before being engulfed by the leading edge 115 that it ceases to be separately viewable by conventional means, such as by viewing the real-time phase change through a microscope. A detector is adapted to view the phase change at portion X before it ceases to become separately viewable, enabling liquid crystal analysis of the die 100 using an internal heat source.

The liquid crystal layer may be formed using methods such as those described in the background hereinabove. According to another example embodiment of the present invention, a liquid crystal emulsion, such as BDH K15 liquid crystal, is placed on the die and formed into a substantially even layer over the die using a blast of air. The air blast is selected such that the volume and flow rate of air make possible the even formation of a liquid crystal layer over the die. By using such an application, the liquid crystal analysis described herein is enhanced.

According to a more particular example embodiment of the present invention, a semiconductor die having an internal heat source and a liquid crystal layer is analyzed. For example, the internal heat source may include an intrinsic heat source present in the die, or a heat source specifically formed for defect analysis. A microscope having a polarized light source, an analyzer, and a camera is arranged over the die. An electrical power source is used to power the die, and the internal heat source generates heat in response. In one implementation, the power source is operated in a continuous loop that includes operational conditions that induce a circuit failure in the die.

The generated heat expands radially and heats other portions of the die including the liquid crystal. As the liquid crystal reaches its transition temperature, it changes phase. The phase change is detectable as a dark area when viewed with the microscope. The phase change of the liquid crystal begins near the intrinsic heat source and expands radially. In connection with this example embodiment, it has been discovered that, as the leading edge of the phase change expansion approaches a defect, the defect heats the portion of the liquid crystal over the defect and causes it to change phase shortly before being engulfed by the leading edge of the phase change resulting from the internal source. If the defect-related liquid crystal phase change occurs at a great enough time interval, it can be detected using real-time analysis, such as by viewing the change through a microscope. If the time interval is too short for real-time analysis, the defect-driven phase change is recorded using the microscope and the camera. The recorded phase change can be used to determine the location of the defect in an altered-time analysis, such as by slow-motion playback.

The type of liquid crystal used can be selected based upon the type of analysis that is to be performed. For example types of liquid crystal material suitable for use in connection with the present invention, reference may be made to T. W. Lee & S. V. Pabbisetty, *Liquid Crystal Microscopy*, in Microelectronic Failure Analysis 141 ($3^{rd}$ ed., ASM International, 1993). Such liquid crystal is available from various sources and can be chosen to provide a state transition temperature (STT) that is just over room temperature for near-room temperature applications. Other liquid crystal material may be used in applications requiring or benefiting from different properties, such as liquid crystal having a STT that is higher or lower for applications where the testing is done at a different temperature.

According to another example embodiment of the present invention, the power supplied to the internal heat source is varied. For example, the power variation may include altering the frequency of the clock cycle being applied to the die. Higher frequencies operate the die at a faster rate and draw more power. Using a constant voltage source, the resulting current draw increases. Advantages of altering the power include enabling the control of the amount of heat generated by the internal heat source. This is useful for controlling the progression of the liquid crystal phase change. For faster advancement of the leading edge of the phase change, the clock is manipulated to cause the intrinsic heat source to generate more heat. For slower advancement of the leading edge, the clock is manipulated to cause the intrinsic heat source to generate less heat. The rate of heat generation can be controlled by increasing or decreasing the frequency of the clock. The power adjustments may, for example, be performed during the analysis process, or may be preset and held constant throughout the analysis process.

In another example embodiment of the present invention, spatial adjustments are made to keep the leading edge of the transition area within the field of view of the microscope. For example, it may be useful to move either the microscope or the die in order to maintain a desired view, particularly when the microscope is focused on a small area of the die. One example manner in which to maintain view of the leading edge of the liquid crystal transition is to mount the die on a moving platform, such as a microscope stage, and move the platform accordingly. Another manner is to move and re-focus the microscope itself on the leading edge of the transition. Still another method is to move both the die and the microscope.

In another example embodiment of the present invention, a cooling arrangement is used to cool the die as it is being analyzed in order to control the intrinsic heating process. For example, the intrinsic heat source may heat the die at such a rate that it is difficult or impossible to sufficiently analyze the die. By cooling the die, the heating rate, and thus the advancement of the leading edge of the transition area, can be slowed or even reversed. Slowing the heating rate helps for defect detection because more time is allowed for obtaining an image of the defect-generated liquid crystal transition before it is engulfed by the leading edge. Reversing the heating rate enables the reversal of the phase transition, allowing the viewing of the defect-generated transition as it transitions back into the original state. One example cooling arrangement includes a filtered compressed gas supply, such as an air supply or a nitrogen supply, adapted to direct the gas at the die.

The cooling arrangement may also be used to speed the analysis process. For example, once the general location of the defect is known, it may be advantageous to heat the die at a fast rate until the leading edge nears the defect. When the defect is neared, the coolant can be used to slow the heat rate and thus slow the expansion of the leading edge as it approaches the defect. Depending upon the die being analyzed, the cooling arrangement can be adjusted to achieve a desired heating rate.

In another example embodiment of the present invention, the heating rate of the die is sufficiently slowed to allow the separate viewing of the phase transition of the liquid crystal using conventional real-time detection methods, such as using a microscope. This enables liquid crystal-assisted defect detection in a die that has an intrinsic heat source located in such proximity to a defect that the heat generated by it overwhelms heat generated at the defect. For instance, when the rate of state change of the liquid crystal is too fast for conventional methods to detect, the power supplied to the die can be altered to reduce the amount of heat supplied, slow the phase change, and allow the real-time viewing of the defect-induced phase change. Similarly, a cooling arrangement such as described hereinabove can be used to cool the die and sufficiently slow the heating (and thus, the state change) of the liquid crystal layer to allow detection of the defect-related state change using conventional methods. In one particular example embodiment, the cooling and heating of the die are controlled in such a manner that the leading edge of the liquid crystal phase transition does not advance. The phase-change advancement is stopped when the defect-related phase transition is present, thereby allowing the static viewing of the defect-generated phase change.

Another manner in which to make the detection of the defect easier is to use the camera to record an image of the liquid crystal phase change as a function of time. The recorded image can, for example, be viewed in slow motion, or viewed in a frame-by-frame mode. Each image (frame) captured by the camera is taken at a sufficiently short time interval that enables the capture of an image of the defect-driven phase change before the leading edge of the intrinsic heat source-driven phase change engulfs the defect. That is, the camera speed must be selected so that each frame is recorded at a time interval that is shorter than the time interval between the occurrence of the defect-driven phase change and the engulfing of the defect-driven phase change by the intrinsic heat-driven phase change.

Figure 2A:
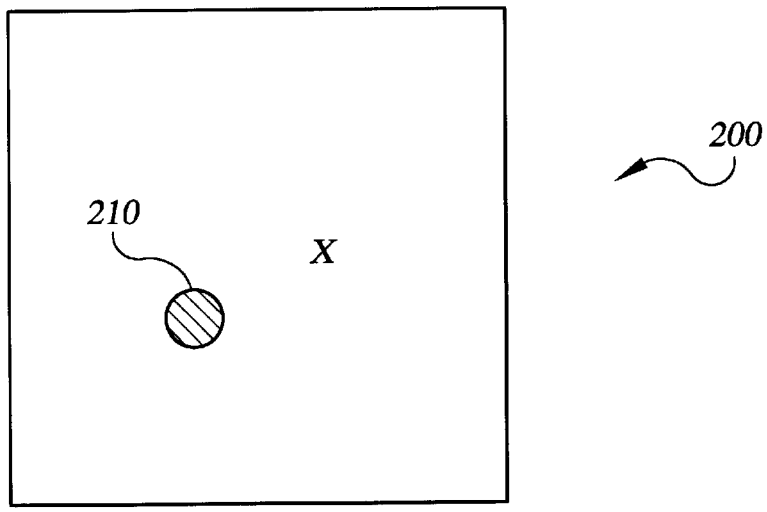
FIG. 2A is a top view of a semiconductor die undergoing analysis, according to another example embodiment of the present invention.
Figure 2B:
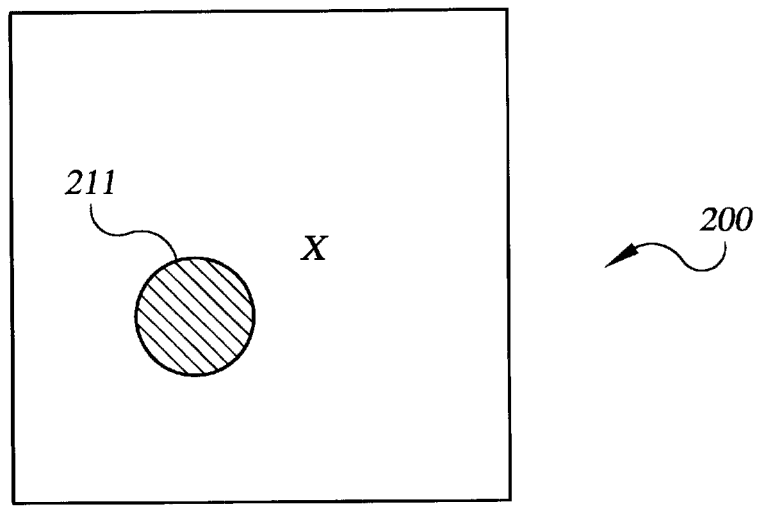
FIG. 2B is a top view of the semiconductor die of FIG. 2A, according to another example embodiment of the present invention.

FIGS. 2A–2D show images of a top view of a liquid crystal layer on a semiconductor die 200 changing phase as a result of heat generated in the die, according to another example embodiment of the present invention. The die 200 includes a defect below the liquid crystal layer, shown as X, and an intrinsic heat source. A microscope is located over the die and is adapted to capture the images shown. The die is electrically stimulated and the intrinsic heat source generates heat that causes a portion 210 of the liquid crystal layer to change phase, as shown in FIG. 2A. As electrical stimulation continues to be applied to the die 200, the portion of the liquid crystal layer that has changed phase expands, shown as portion 211 in FIG. 2B.

Figure 2C:
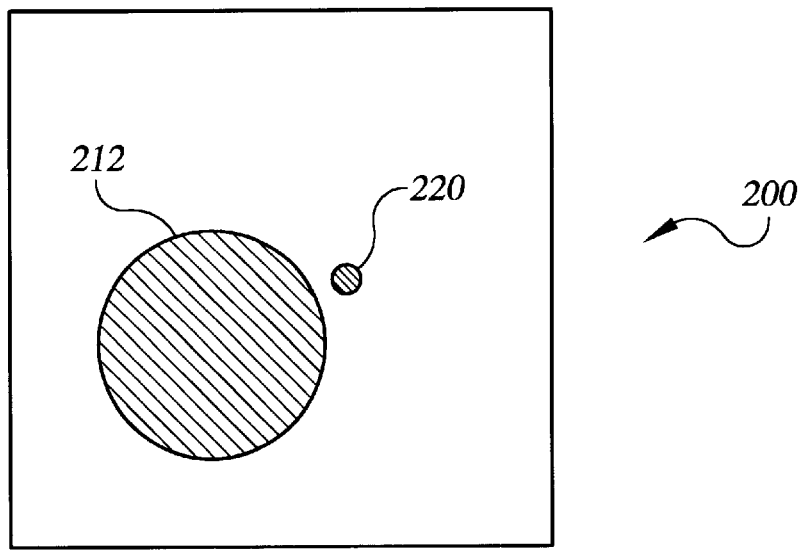
FIG. 2C is a top view of the semiconductor die of FIG. 2A, according to another example embodiment of the present invention.
Figure 2D:
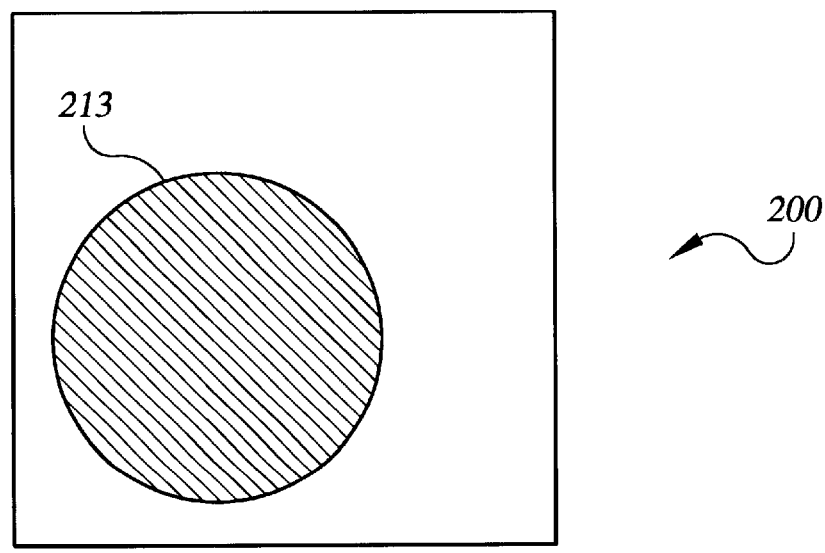
FIG. 2D is a top view of the semiconductor die of FIG. 2A, according to another example embodiment of the present invention.

In addition to the heat generated by the intrinsic heat source, the defect also generates heat. In FIG. 2C, the expanding area of liquid crystal having undergone a phase change 212 has nearly reached the portion of liquid crystal over the defect. At this point, the combined heat generated by the intrinsic heat source and the defect is sufficient to cause a portion 220 of the liquid crystal to change phase. The microscope is used to capture the image of this phase change before the expanding area engulfs the portion 220, as shown in FIG. 2D.

Referring again to FIGS. 2C and 2D, and according to another example embodiment of the present invention, a cooling arrangement is used to reverse the phase transition, such as described herein above. If the transition to FIG. 2D occurs too fast, the application of a cooling arrangement can be used to reverse the transition so that the phase transition regresses to the image shown in FIG. 2C. In this manner, the defect can be detected even if the advancement of the phase transition is too rapid for analysis without a cooling arrangement. In addition, the power supply to the die can also be adjusted to control the amount of heat generated in the die and to enable the regression of the liquid crystal phase change from FIG. 2D to FIG. 2C. The power adjustment can be used alone or in conjunction with the cooling arrangement to achieve the desired result.

Figure 3:
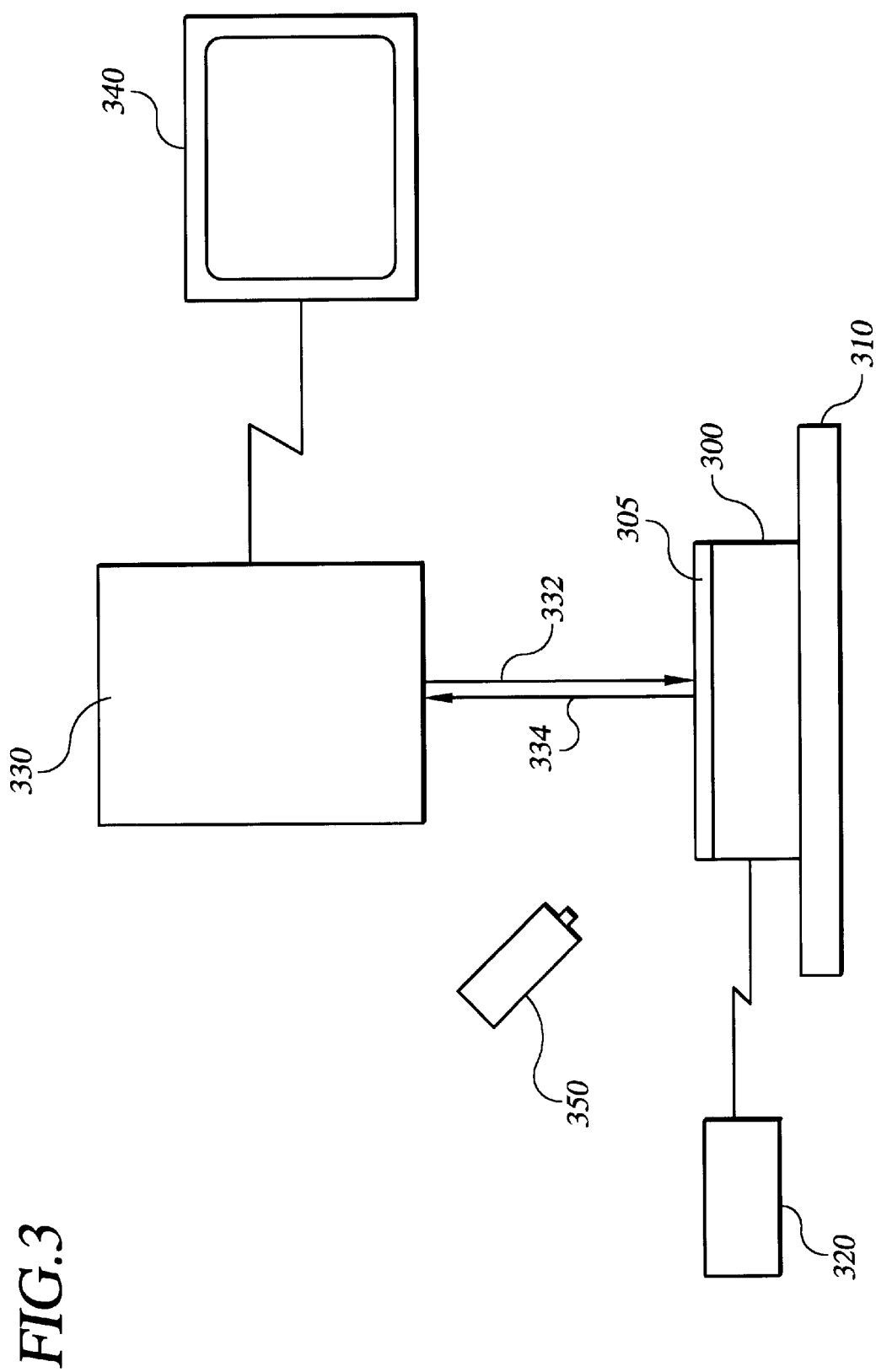
FIG. 3 is a system for analyzing a semiconductor die, according to another example embodiment of the present invention.

FIG. 3 is a system adapted to detect a defect using a liquid crystal phase change, according to another example embodiment of the present invention. The system may, for example, be used to create the images shown in FIGS. 2A–2D. The system includes a mounting platform 310 adapted to hold a semiconductor die 300 having a liquid crystal layer 305 and an intrinsic heat source. A power supply 320 is coupled and adapted to supply power to the die and to generate heat in the die via the intrinsic heat source. A detection arrangement 330 is arranged over the liquid crystal layer 305 and is adapted to capture an image of the liquid crystal as it changes phase due to heat generated by a defect and by the intrinsic heat source. A polarized light source is adapted to direct polarized light 332 at the die 300. An analyzer (linear polarizer) is arranged so that an image 334 from the die 300 passes through it before it is captured. The defect-related phase change occurs momentarily before a phase change generated by the intrinsic heat source in the die, such as discussed hereinabove. The detection arrangement 330 is adapted to capture the image before the defect-related phase change ceases to be separately viewable from the phase change caused by the intrinsic heat source.

The detection arrangement optionally includes a monitoring arrangement 340 adapted to display an image of the phase change of the liquid crystal layer 305. In one implementation, the monitoring arrangement includes a video recorder adapted to receive the image data captured by the detection arrangement 330. The video recorder can be used to display the image data in slow motion or frame-by-frame mode to facilitate the viewing of the defect-generated phase change.

In another example embodiment, the power supply 320 is further adapted to modulate the amount of heat generated in the die. For example, altering the clock frequency as described hereinabove causes the die to speed up and generate more heat. The additional power supplied alters the amount of heat generated in the die, and can be chosen to correspond with the type of intrinsic heat source that is in the die.

In another instance, the system further includes a cooling arrangement 350. The cooling arrangement is adapted to cool the die and to control the advancement of the phase change of the liquid crystal layer. For example, the cooling arrangement can be used to supply a gas, such as compressed air or nitrogen. A filter (not shown) is adapted to remove particulates from the gas, and may be included in the filter arrangement or be located externally to the cooling arrangement. The cooling arrangement may be used alone or in conjunction with altering the power supply to the die for controlling the advancement of the liquid crystal phase change.

Figure 4:
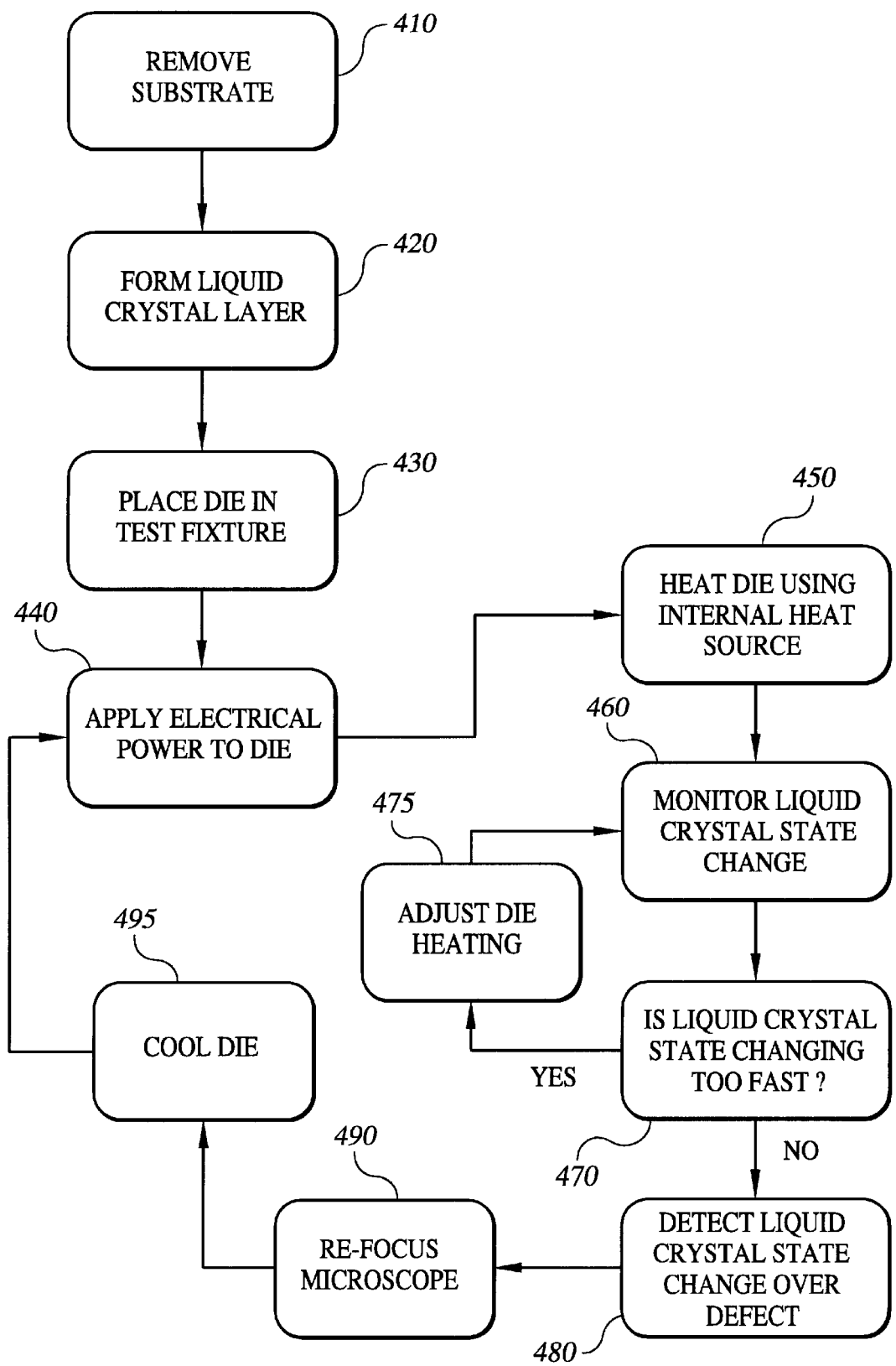
FIG. 4 is a flow diagram of a method for using the system of FIG. 3 for analyzing a semiconductor die, according to an example embodiment of the present invention.

FIG. 4 is a flow diagram of a method for analyzing a semiconductor die using a system, such as the system in FIG. 3, according to another example embodiment of the present invention. Where substrate must first be removed to facilitate sufficient heat transfer to the surface, a substrate removal device is used to remove a portion of substrate from a semiconductor die having an internal heat source at block 410. After the portion of substrate has been removed, a liquid crystal layer is formed on a region exposed by the substrate removal at block 420. For example, adding a solvent such as pentane to liquid crystal and using a deposition arrangement, such as a syringe, to deposit the liquid crystal on the die will form a sufficient liquid crystal layer. A liquid crystal emulsion can also be used and applied using an air blast, such as described hereinabove. Other solvents and/or various types of liquid crystal may also be used.

After the liquid crystal layer is formed, the die is placed in a test fixture at block 430, and powered at block 440. In response to the supplied power, the internal heat source generates heat at block 450. At block 460, the liquid crystal layer is monitored for a state change in response to the generated heat. If the liquid crystal state is changing too fast at block 470, the die heating is adjusted at block 475. The adjustment may include, for example, altering the power supply or using a cooling device to cool the die. Once the adjustment is made, the process continues at block 460.

If the liquid crystal state is not changing too fast at block 470, a liquid crystal state change is detected at block 480. The state change detected is due at least in part to heat generated at a defect in the device, and is detected as a state change that occurs momentarily before the state change being driven by the internal heat source. The detection may include, for example, capturing video images of the state change at an image capture interval sufficiently short to enable the viewing of the defect-generated state change prior to it being engulfed by the intrinsic heat source-driven state change.

In another alternate example embodiment using a microscope to monitor the liquid crystal state change, the microscope is re-focused at block 490 after the state change is detected at block 480. After the microscope is refocused, the die is allowed to cool sufficiently at block 495 so that the liquid crystal phase change regresses to allow the defect-generated phase change to be detected, and the process continues at block 440. In this manner, the location of the defect can be generally detected, and then subsequently more specifically located using the refocused microscope.

In another example embodiment of the present invention, after the defect-related state change has been detected at block 480, the microscope is focused on the defect so that the position of the defect in a viewed image through the microscope is easily determined. The die being analyzed is then removed from the test fixture. While maintaining the microscope in the same position and focus, another die having similar structure to the die being analyzed and having a portion of the circuitry exposed is placed in the test fixture. The exposed circuitry can then be viewed and, using the known position of the defect in the viewed image, the portion of circuitry having a defect is determined.

In still another example embodiment, discovered in connection with the present invention, a laser-scanning microscope (LSM) can be used to peer through the liquid crystal layer and image the circuitry. By forming the liquid crystal layer at a distance of about 80 microns or less over the circuitry, the image of the defective circuitry can be obtained with the die being analyzed. When the liquid crystal layer is formed at a distance of about 5–10 microns over the circuitry, other commonly-available microscopes can be used to image the circuitry. Accordingly, using this example embodiment in connection with FIG. 4, after the liquid crystal state change has been detected at block 480, the circuitry below the liquid crystal layer is imaged. In this manner, the particular circuitry below the defect-generated phase change can be detected.

While the present invention has been described with reference to several particular example embodiments, those skilled in the art will recognize that many changes may be made thereto without departing from the spirit and scope of the present invention, which is set forth in the following claims.

What is claimed is:

1. A method for analyzing a semiconductor die, the method comprising:
   forming a liquid crystal layer on the die;
   electrically operating a first circuit region in the die and using heat from the first circuit region as a primary heat source to generate sufficient heat at a second circuit region to effect a separately-detectable phase change in an area of the liquid crystal layer corresponding to the second circuit region; and
   detecting the liquid crystal phase change in the area corresponding to the second circuit region.

2. The method of claim 1, wherein detecting the liquid crystal phase change in the area corresponding to the second circuit region includes using a detector adapted to detect the liquid crystal phase change in the area corresponding to the second circuit region using time-lapsed analysis.

3. The method of claim 1, wherein the electrical operation is adapted to generate sufficient heat to effect the phase change without applying an external heat source to the die.

4. The method of claim 1, wherein the first and second circuit regions are selected so that the phase change corresponding to the second circuit region ceases to be separately viewable by real-time analysis.

5. The method of claim 4, wherein the selecting the first and second regions so that the corresponding phase changes cease to be separately viewable by real-time analysis includes selecting the first and second regions so that the corresponding phase changes cease to be separately viewable by a human eye viewing the image via a microscope.

6. The method of claim 1, wherein detecting the liquid crystal phase change includes arranging a microscope having a polarized light source and an analyzer to view the semiconductor die.

7. The method of claim 6, wherein a camera is used to record an image of the die as a function of time, the image being indicative of the liquid crystal changing phase.

8. The method of claim 1, wherein detecting the liquid crystal phase change in the area corresponding to the second region includes detecting a defect in the second circuit region.

9. The method of claim 1, further comprising forming the liquid crystal layer over at least a portion of the semiconductor die.

10. The method of claim 9, further comprising thinning a portion of the integrated circuit prior to forming the liquid crystal layer.

11. The method of claim 1, wherein electrically operating the first circuit region includes operating the die in a continuous loop that includes operational conditions that induce a circuit failure at the second circuit region.

12. The method of claim 1, wherein electrically operating the first circuit region includes adjusting the frequency used to electrically operate the first circuit region.

13. The method of claim 6, further comprising moving the microscope to keep a boundary of the expanding intrinsic transition area within the field of view of the microscope.

14. The method of claim 7, further comprising viewing the recorded image in slow motion.

15. The method of claim 6, further comprising:
   ceasing to electrically operate the first circuit region and allowing the liquid crystal to sufficiently cool to transition back into its original phase;
   increasing the magnification of the microscope and focusing on selected area; and
   repeating the steps of electrically operating the first circuit region and detecting the liquid crystal phase change.

16. The method of claim 1, further comprising cooling the die to control the rate of phase change so that the phase changes are separately viewable.

17. The method of claim 16, wherein cooling the die includes directing a cooling agent at the die, the cooling agent comprising at least one of: compressed air and compressed nitrogen.

18. The method of claim 17, further comprising filtering the cooling agent prior to cooling the die.

19. The method of claim 16, wherein cooling the die includes causing the phase change to slow down.

20. The method of claim 16, wherein cooling the die includes causing at least a portion of the liquid crystal having undergone a phase change to change back into its original phase.

21. The method of claim 16, wherein cooling the die is used in conjunction with altering the power supply to the die to control the rate of liquid crystal phase change.

22. The method of claim 1, further comprising using a laser-scanning microscope to image the second circuit region through the liquid crystal layer.

23. The method of claim 6, further comprising:
   focusing the microscope so that the defect-generated phase change is locatable in an image obtained with the microscope;
   replacing the semiconductor die with a structurally similar die having a circuit region exposed; and
   without adjusting the microscope, detecting the defective circuitry by locating the circuitry corresponding to the location of the defect-generated phase change.

24. The method of claim 1, wherein forming a liquid crystal layer comprises placing liquid crystal emulsion material on a surface of the die and directing an air blast at the emulsion sufficient to cause the emulsion to spread evenly over the surface.

25. The method of claim 1, wherein electrically operating the first circuit region includes electrically operating an intrinsic heat source.

26. The method of claim 1, further comprising forming an internal heat source in the die, wherein the first circuit region includes the internal heat source.

27. The method of claim 26, wherein the internal heat source is formed to selectively heat a portion of the die.

28. A system for analyzing a semiconductor die having a liquid crystal layer, the system comprising:
   means for electrically operating a first circuit region in the die and using heat from the first circuit region as a primary heat source to generate sufficient heat at a second circuit region to effect a separately detectable phase change in an area of the liquid crystal layer corresponding to the second circuit region; and
   means for detecting the liquid crystal phase change in the area corresponding to the second circuit region.

29. A system for analyzing a semiconductor die having a liquid crystal layer, the system comprising:
   a power source adapted to electrically operate a first circuit region in the die and using heat from the first circuit region as a primary heat source to generate sufficient heat at a second circuit region to effect a separately detectable phase change in an area of the liquid crystal layer corresponding to the second circuit region; and
   a detection arrangement adapted to detect the liquid crystal phase change in the area corresponding to the second circuit region.

30. The system of claim 29, wherein the detection arrangement includes a microscope.

31. The system of claim 30, wherein the microscope includes a polarized light source and an analyzer.

32. The system of claim 31, further comprising a camera adapted to capture an image from the microscope, the captured image being indicative of the liquid crystal changing phase.

33. The system of claim 32, further comprising a recorder adapted to record the captured image of the die as a function of time.

34. The system of claim 29, further comprising a cooling arrangement adapted to cool the die and slow the rate of phase change.

35. The system of claim 34, wherein the cooling arrangement includes at least one of: a compressed air supply and a compressed nitrogen supply.

36. The system of claim 35, further comprising a coolant supply filter adapted to filter particulates from coolant material.

37. The system of claim 29, wherein the power source is adapted to control the rate of heating of the die.

38. The system of claim 37, wherein the power source is adapted to control the rate of heating of the die responsive to the input clock frequency.

39. The system of claim 29, wherein the detection arrangement is adapted to move in order to keep a boundary of the phase change effected by the first circuit region within its field of view.

40. The system of claim 33, wherein the recorder is adapted to play the recorded image in slow motion for viewing.

41. The system of claim 29, further comprising a liquid crystal deposition arrangement adapted to form the liquid crystal layer on the die.

42. The system of claim 41, further comprising a substrate removal device adapted to remove a portion of substrate from the die prior to forming the liquid crystal layer.

43. The system of claim 29, wherein the detection arrangement is further adapted to detect the liquid crystal phase change when the first and second circuit regions cease to be separately detectable by real-time analysis.

* * * * *

UNITED STATES PATENT AND TRADEMARK OFFICE
CERTIFICATE OF CORRECTION

PATENT NO. : 6,599,762 B1 Page 1 of 1
DATED : July 29, 2003
INVENTOR(S) : Eppes

It is certified that error appears in the above-identified patent and that said Letters Patent is hereby corrected as shown below:

Column 5,
Line 6, "circuit regions 10" should read -- circuit regions 110 --.
Line 8, "circuit regions 10" should read -- circuit region 110 --.

Signed and Sealed this

Twenty-fifth Day of November, 2003

JAMES E. ROGAN
*Director of the United States Patent and Trademark Office*